United States Patent
Cesti et al.

(10) Patent No.: US 6,992,214 B2
(45) Date of Patent: Jan. 31, 2006

(54) INTEGRATED PROCESS FOR THE PREPARATION OF AROMATIC ISOCYANATES AND PROCEDURES FOR EFFECTING THE RELATIVE INTERMEDIATE PHASES

(75) Inventors: Pietro Cesti, Trecate-Novara (IT); Aldo Bosetti, Vercelli (IT); Franco Mizia, Milan (IT); Marcella Notari, Parma (IT); Marco Ricci, Novara (IT); Franco Rivetti, Milan (IT); Ugo Romano, Vimercate (IT)

(73) Assignee: Dow Global Technologies Inc., Midland, MI (US)

(*) Notice: Subject to any disclaimer, the term of this patent is extended or adjusted under 35 U.S.C. 154(b) by 99 days.

(21) Appl. No.: 10/220,593

(22) PCT Filed: Feb. 1, 2001

(86) PCT No.: PCT/EP01/01056

§ 371 (c)(1),
(2), (4) Date: Mar. 17, 2003

(87) PCT Pub. No.: WO01/56977

PCT Pub. Date: Aug. 9, 2001

(65) Prior Publication Data

US 2003/0162995 A1 Aug. 28, 2003

(30) Foreign Application Priority Data

Feb. 3, 2000 (IT) .................................... MI2000A0165

(51) Int. Cl.
*C07C 263/04* (2006.01)

(52) U.S. Cl. ..................................................... 560/345
(58) Field of Classification Search ................. 560/345, 560/336

See application file for complete search history.

(56) References Cited

U.S. PATENT DOCUMENTS 4,290,970 A * 9/1981 Merger et al. ............... 560/345

FOREIGN PATENT DOCUMENTS

| EP | 0 323514 | * | 7/1999 |
| WO | 98 56758 | * | 12/1998 |
| WO | 99 047493 | * | 9/1999 |

* cited by examiner

*Primary Examiner*—Emily Bernhardt
*Assistant Examiner*—Ebenezer Sackey

(57) ABSTRACT

Integrated process for the preparation of aromatic isocyanates comprising: the reaction between an aromatic amine and an organiccarbonate in the presence of a catalyst selected from organic and inorganic salts of a metal selected from Zn, Sn, Pb, Cu; the removal of the catalyst; the passivation of the quantity of residual metal in the urethane formed in step a); the removal of the organic solvent and its optional recycling to step a) of the reaction; the evaporation of the aromatic urethane with partial pyrolysis; the complete pyrolysis of the urethane in gas phase; the recovery of the isocyanate.

16 Claims, 3 Drawing Sheets

INTEGRATED PROCESS FOR THE PREPARATION OF AROMATIC ISOCYANATES AND PROCEDURES FOR EFFECTING THE RELATIVE INTERMEDIATE PHASES

The present invention relates to a process for the preparation of aromatic isocyanates consisting in the conversion of an aromatic amine into the corresponding urethane by reaction with an organic carbonate, in the presence of a suitable catalyst, and in the subsequent thermal decomposition of the urethane groups into isocyanate, after an intermediate series of operations such as the removal of the catalyst, the passivation of the metal residues in the urethane, and the evaporation of the latter; the invention also relates to the specific procedures for effecting these intermediate phases.

The preparation of isocyanates starting from the reaction between amines and organic carbonates is known.

For example, U.S. Pat. No. 5,315,034 describes a multistep process for the preparation of alkyl mono and diisocyanates consisting in reacting acting the corresponding aliphatic amine or diamine with dimethylcarbonate and, substantially, in vaporizing and partially converting the urethane thus formed in an evaporator, subsequently terminating the cracking in a second reactor, and finally subjecting the cracking product to fractionated distillation at reduced pressure, with recycling of the non-converted part to the partial vaporization step; in the first phase a base catalyst is used, consisting of alcoholates of alkaline or earth-alkaline metals: the process allows alkyl mono and diisocyanates to be obtained with good yields, but is strictly limited to these and it does not seem that the disclosure can be easily extended to aromatic isocyanates.

The process described in International patent application WO 98/56758 proposes a widening in the spectrum of isocyanates prepared without the use of toxic agents and essentially consists in the reaction between an amine and an organic carbonate in the presence of a catalyst and organic solvent, the removal of the catalyst, the thermal decomposition of the carbamate formed and final distillation of the solvent/alcohol mixture.

The process however does not seem to be of industrial interest as it has a low productivity owing to the fact that the thermal decomposition is carried out in a solvent under dilute conditions.

The Applicant has now found that by using a well defined group of metal catalysts and operating conditions in the initial reaction between aromatic amine and organic carbonate, by specifically treating the metal residues present in the urethane after the normal removal of the catalyst and causing the pyrolysis of the urethane in gas phase, after its evaporation, it is possible to obtain high productivities of aromatic isocyanates with a high degree of selectivity.

A first object of the present invention in fact relates to an integrated process for the preparation of aromatic isocyanates comprising:
a) the reaction between an aromatic amine and an organic carbonate in the presence of a catalyst selected from organic and inorganic salts of a metal selected from Zn, Sn, Pb, Cu;
b) the removal of the catalyst;
c) the passivation of the residual quantities of metal in the urethane formed in step a);
d) the removal of the solvent and its optional recycling to step a) of the reaction;
e) the evaporation of the aromatic urethane with partial pyrolysis;
f) the complete pyrolysis of the urethane in gas phase;
g) the recovery of the isocyanate.

Figure 1:
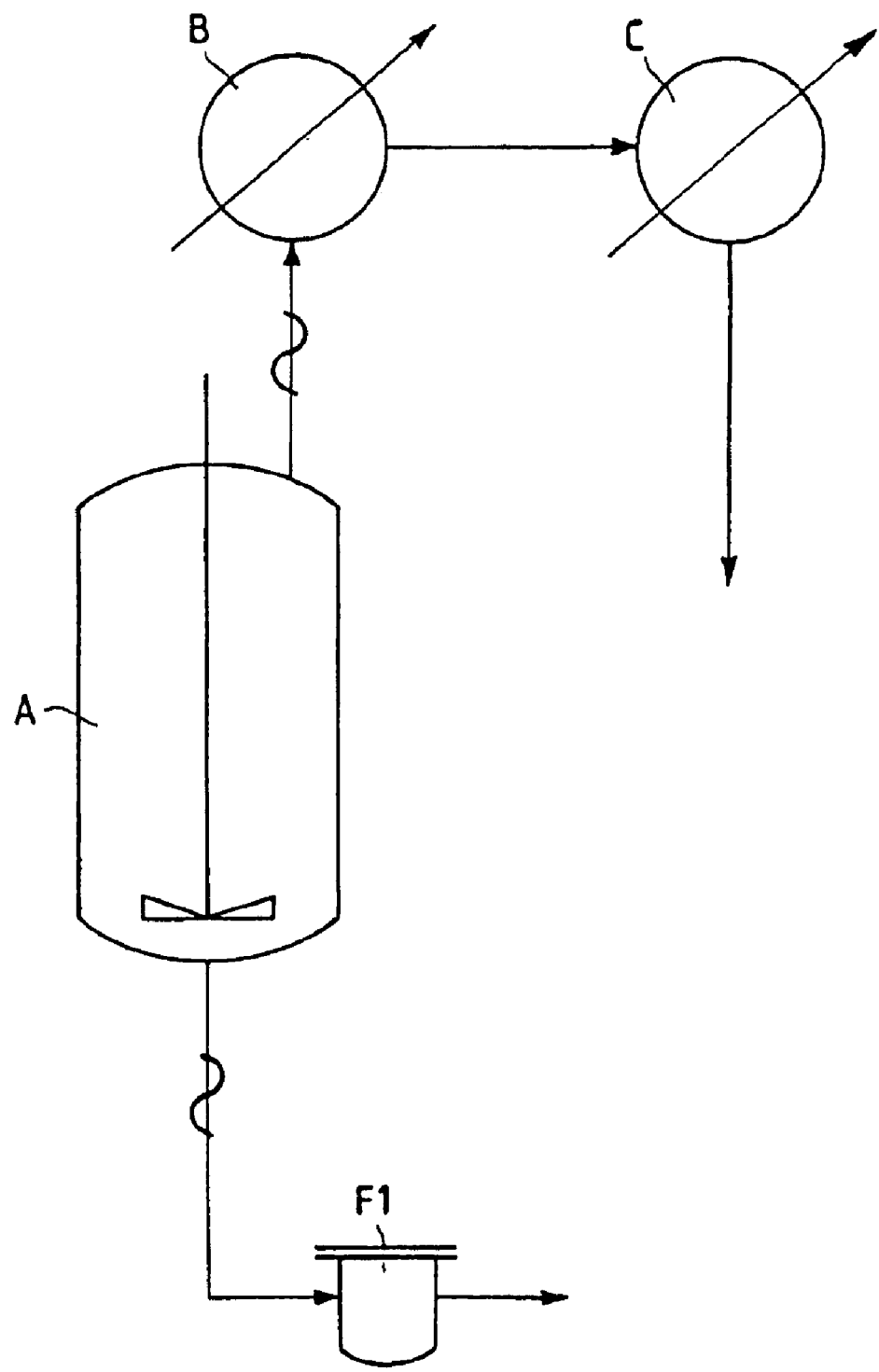
FIG. 1 is a representation of equipment for synthesis of a diamine from a diurethane.

The process for the preparation of aromatic isocyanates according to the present invention can be described in detail as follows.

In the first step, the process for the synthesis of aromatic urethanes comprises:

reacting an organic carbonate in stoichiometric quantities, or higher than the stoichiometric value, with an amine having formula (I):

$$R\text{—}(NH_2)_n \qquad (I)$$

wherein n is an integer ranging from 1 to 2, R represents an aryl radical, such as monovalent, bivalent radicals of benzene, toluene, naphthalene, diphenyl, methylenediphenyl.

The aryl radical can contain, as substituents, one or more alkyl radicals having from 1 to 4 carbon atoms.

The aryl radical can contain, as substituents, atoms or radicals which are non-reactive with the isocyanate function, such as halogen atoms, alkoxy, nitro, cyano, acyl, acyloxy, isocyanate groups.

Non-limiting examples of aromatic amines having formula (I) are: 2,4-diaminotoluene, 2,6-diaminotoluene or mixtures of the two isomers, aniline, toluidine, 3,5-dichloroaniline, 4,4'-methylenedianiline, 2,4'-methylenedianiline, 2,2'-methylenedianiline or mixtures of isomers.

The reaction is carried out in the presence of a catalyst selected from organic or inorganic salts, of a metal selected from Zn, Sn, Pb, Cu: various salts are used. Among these however anhydrous or dihydrate zinc carboxylates, base carbonates of copper, base carbonates of zinc, mixed carbonates of zinc and copper, zinc carbamates, are preferred.

The alcohol which is formed during the reaction is continuously removed by distillation, maintaining inside the reaction mixture a quantity thereof ranging from 10 to 40% with respect to the total co-product.

Organic carbonates which can be used in the process are alkyl esters of carbonic acid. The ester group contains an alkyl group with up to 6, preferably up to 4, carbon atoms. Examples of particularly suitable organic carbonates are dimethyl carbonate, diethyl carbonate, dipropyl carbonate. The organic carbonates can be prepared using the known methods. The quantity of carbonate used varies from the stoichiometric value with respect to the amine groups contained in the molecules having formula (I), to an excess quantity, as the carbonate can be used as solvent.

Any solvent can be used provided it is inert with the reagents under the operating conditions. Mixtures of suitable solvents can also be used.

The solvents can be selected from alkylated and non-alkylated aromatic hydrocarbons, such as for example, benzene, toluene, xylene; aromatic hydrocarbons containing functional groups inert with the reagents, such as for example, anisole, benzonitrile, chlorobenzene, dichlorobenzene; alkanes and alkanes containing functional groups inert with the reagents, such as for example, cyclohexane, n-heptane, n-hexane, dichloromethane, diethylether, acetonitrile, dioxane.

The quantity of catalyst can vary from 20 to 0.5% in moles, preferably from 10 to 1.0% in moles per mole of amine (I). The reaction temperature can vary from 100 to 200° C., preferably from 140–180° C., and can be kept constant or increased within the above range, during the reaction.

The reaction is carried out at an operating pressure or autogenous pressure of the system, or in any case ranging from 2 to 15 absolute atm., preferably from 3 to 7 absolute atm.

The reaction time is in relation to the temperature and pressure: however, reaction times ranging from 1 to 5 hours have proved adequate.

The reaction proceeds until the complete, or substantially complete, conversion of the amine groups to form a mixture of aromatic urethane and alcohol, this being removed alone or in a mixture with the excess organic carbonate, and the mixture is separated according to the conventional techniques, with the possible organic carbonate which is recycled to be fed again to the formation reaction of urethane.

The catalyst is subsequently removed, using for the purpose any method known to experts in the field. It has also proved to be particularly advantageous to remove the catalyst, after the addition of water, according to a procedure which, as it represents an important aspect of the process for the preparation of aromatic isocyanates according to the present invention, forms a second object thereof, thus characterizing a very particular process for the preparation of aromatic urethanes.

The addition of water allows the metal residues, which accompany the urethane after filtration, to be kept within quantities of less than 20 ppm, with obvious advantages considering that the traditional methods for the removal of catalysts do not reduce the metal residues in the urethane to below 500÷1000 ppm.

The water, in quantities ranging from 0.5:1 to 10:1 moles of water per mole of catalyst initially charged, preferably from 1:1 to 4:1 moles, is added directly to the reaction mixture at temperatures ranging from 100 to 200° C., preferably from 110 to 160° C., at pressures ranging from 2 to 15 absolute atm., preferably from 3 to 7 absolute atm.

A second important object of the present invention therefore relates to a process for the synthesis of aromatic urethanes which comprises reacting an organic carbonate and an aromatic amine, according to the terms and conditions described above, in the presence of one of the above-mentioned catalysts or other metal derivatives, and which is characterized by the addition of water to remove the catalyst before the recovery of the urethane formed.

The conditions of the addition of water, in the above process for the preparation of aromatic urethanes, are those which have just been described in relation to this procedure when selected as step b) of the process for the preparation of aromatic isocyanates according to the present invention.

With reference to this process, it is important, for effecting the subsequent steps and obtaining results which are industrially interesting, for the urethane obtained after the removal of the catalyst to be subjected to a particular treatment to enable the final thermal treatment to be carried out, reducing to the minimum the effect of side-reactions such as decarboxylation of the urethane with the formation of an amine; the reaction between the amine and isocyanate produced with the formation of ureas, the reaction between the isocyanate produced and the starting urethane with the formation of allophanates and polymeric products.

The undesired reactions which result in the formation of these by-products are so strongly favoured by the presence in the starting urethane of metal catalytic residues, deriving from the production reaction of the urethane itself, as to cause fouling of the equipment necessitating interruption of the processing.

According to the present invention, it has been unexpectedly found that it is possible to evaporate with partial pyrolysis and to pyrolyze in gas phase the aromatic urethanes containing catalytic residues, with high yields and high selectivities to isocyanates after stabilizing treatment with phosphoric acid or oxalic acid: this process has a general significance, and forms a third object of the present invention, in that it is an important step in the process for the preparation of aromatic isocyanates.

More specifically, the procedure for the production of aromatic isocyanates is characterized in that aromatic urethanes containing catalytic residues are dissolved in a low-boiling solvent, present in a weight ratio with respect to the urethane ranging from 1:1 to 10:1, preferably from 2:1 to 6:1 and are treated with phosphoric acid in a molar ratio of the latter with respect to the metal, present as catalytic residue, ranging from 1:1 to 10:1 and preferably from 1:1 to 3:1 at a temperature ranging from 100° C.–150° C., preferably from 120° C. to 140° C., at a pressure ranging from 2 to 15 absolute atm., preferably from 3 to 7 absolute atm., for a period of time ranging from 0.5 to 4 hours, preferably from 1 to 2 hours.

The treatment can be carried out directly on the solution of urethane coming from the synthesis, after separation of the catalyst (step b).

At the end of the treatment, the solvent is eliminated by distillation at reduced pressure. Examples of solvents are: dimethylcarbonate, diethylcarbonate, tetrahydrofuran, dioxane, acetonitrile, methanol, ethanol; the solvent in which the synthesis reaction of urethane is effected, is preferred.

The treated urethane is then subjected to evaporation and pyrolysis in gas phase.

With reference to the process in question, at the end of the passivation procedure of the catalyst, the solvent is removed by distillation in an apparatus consisting of one or more evaporators, which operate with short contact times, at a temperature ranging from 100° C. to 200° C., preferably from 150° C. to 180° C., at a pressure ranging from 3 to 0.2 absolute atm., preferably from 2 to 0.5 absolute atm.

The solvent recovered is optionally recycled to the synthesis reaction of step a) and the aromatic urethane, in accordance with the process for the preparation of aromatic isocyanates according to the present invention, is subjected to evaporation with partial pyrolysis and to subsequent pyrolysis in gas phase. The above-mentioned procedure, which, when applied to the process according to the present invention, represents the concluding phase, can, in turn, form a further significant object of the present invention as it represents, in general terms, a procedure for the preparation of aromatic isocyanates by means of the pyrolysis of the corresponding urethanes, however obtained, said procedure consisting in subjecting the urethanes in molten state or in solution, to thermal treatment under such conditions of temperature and pressure as to allow the evaporation and partial conversion into isocyanates and, subsequently subjecting the vapors to a second thermal treatment in a pyrolysis reactor, which operates at a higher temperature or at a value however that is sufficient to complete the conversion of the urethane.

It is evident that the combined effect of the evaporation of the urethane and its subsequent pyrolysis would be much more significant if the urethane had been previously subjected to the above passivation treatment of the catalytic residues.

The vapor leaving the pyrolysis reactor, which contains alcohol and isocyanate, is subjected to fractionated condensation to separate its constituents.

Compared with the known methods, the process described above allows isocyanates to be obtained with a high volume/time yield and a high selectivity, using a method which can be easily industrialized, allowing operation in continuous.

More specifically, the procedure for the production of isocyanates having formula III is characterized in that urethanes having formula II are thermolithically cracked according to the following equation:

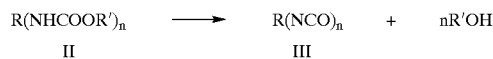

$$R(NHCOOR')_n \longrightarrow R(NCO)_n + nR'OH$$
$$\text{II} \qquad\qquad\qquad \text{III}$$

wherein n and R have the same values and meanings as formula I; R' represents an aliphatic organic radical, containing from 1 to 6 carbon atoms, preferably containing from 1 to 4 carbon atoms.

Typical examples of urethanes which are pyrolyzed in the process of the present invention are: 2,4-toluene dimethylurethane, 2,6-toluene dimethylurethane, mixtures of 2,4-toluene dimethylurethane and 2,6-toluene dimethylurethane, N-phenylmethylurethane, N-phenylethylurethane, 4-methylphenylethylurethane, 3,5-dichloro phenylethylurethane, 4,4'-methylene bis (phenylmethylurethane), 2,4'-methylene bis (phenylmethylurethane), 2,2'-methylene bis(phenylmethylurethane) or mixture of isomers.

An object of the present invention therefore also relates to a process for the preparation of aromatic isocyanates by the pyrolysis of urethanes in gas phase, characterized in that urethanes in the molten state, or in solution with an inert high-boiling solvent, are fed to a first pyrolysis reactor, which causes the partial or total evaporation of the urethane fed and a partial pyrolysis thereof, operating at a temperature within the range of 230° C.–380° C., preferably within the range of 270° C.–320° C., at a pressure within the range of 1 to 300 mmHg, preferably within the range of 20–150 mmHg.

The liquid urethane is fed to the first pyrolysis reactor with a LSHV space velocity ranging from 0.2 to 4 hours$^{-1}$, preferably from 0.5 to 2 hours$^{-1}$.

The mixture of vapors leaving the first reactor, which contains in addition to the starting urethane, also pyrolysis products, is fed to the second pyrolysis reactor which operates at a temperature ranging from 300° C. to 600° C., preferably from 350° C. to 550° C. and is in equi-pressure with the first pyrolysis reactor.

The feeding of the vapors to the second cracking reactor takes place with a GHSV space velocity, under normal conditions, ranging from 20 to 500 hours$^{-1}$, preferably from 40 to 200 hours$^{-1}$.

The mixture of vapors leaving the second cracking reactor is subjected to fractionated condensation, with a first condensation at a temperature within the range of 10° C.–150° C., preferably within the range of 20° C.–100° C., allowing a fraction containing the desired isocyanate to be obtained, and a second condensation at a temperature within the range of −80° C. to +50° C., preferably within the range of −30° C. to +10° C. from which a fraction mainly containing alcohol is obtained.

The high-boiling inert solvent, which optionally dilutes the liquid urethane fed, can be present in a weight ratio with respect to the urethane ranging from 3/1 to 0.01/1, preferably from 0.3/1 to 0.05/1.

The solvent must be inert under the reaction conditions, it should have a boiling point higher than that of the urethane and preferably has good solvent properties for the urethane.

Examples of these solvents are: substituted or non-substituted aromatic hydrocarbons such as polyphenyls, triphenyl, tetraphenyl, dodecylbenzene, dibenzyltoluene, polyphenylether, methylnaphthalene, benzylnaphthalene, dichloronaphthalene, esters of organic acids such as dibutylphthalate, dioctylphthalate, sulfones such as diphenylsulfone, phenyltolylsulfone, naphthylphenylsulfone.

The first pyrolysis reactor can be a fine film evaporator in which, with the supply of an appropriate quantity of heat, the product fed can be completely vaporized and already partially converted to isocyanate; or, preferably, a fraction mainly containing urethane can be discharged from the bottom to obtain a solvent effect on the small quantity of polymeric products present. The ratio between vaporized product and product collected at the bottom ranges from 70:30 to 99:1, preferably from 80:20 to 95:5.

In an embodiment of the invention, the product collected at the bottom, after separation from the pitches, is re-fed to the first pyrolysis reactor. The separation of the pitches is carried out by extraction of the urethane in a solvent in which the pitches are insoluble, or by evaporation of the urethane in a subsequent apparatus in which the pitches are collected at the bottom.

Examples of solvents which can be used for the extraction of the urethane are: methanol, ethanol, propanol, butanol, acetonitrile, tetrahydrofuran, dioxane, chloroform, methylene chloride, methylpyrrolidone. The preferred solvent is the alcohol corresponding to the R' alkyl group in formula (II) of urethane.

If the urethane, fed to the film evaporator, is diluted in a solvent with a boiling point higher than that of the urethane, the molten liquid, discharged from the bottom, mainly contains the solvent which, after separation from the polymeric products, can be optionally recovered.

The second pyrolysis reactor is generally a quartz or inox steel, cylindrical, tubular reactor. This reactor can be used empty or filled with heat-resistant material, such as steel chips or rings or other fillings known in the art, which however have the effect of improving the heat transfer.

The aromatic isocyanate obtained is recovered from the condensed fraction in which it is contained as main product in a concentration normally ranging from 80% to 99% by weight, by means of continuous or semi-continuous distillation in an apparatus consisting of an evaporator, which operates with short contact times, and a column.

This apparatus operates at a temperature within the range of 60° C.–200° C., preferably within the range of 90° C.–150° C. and at a pressure within the range of 1 to 200 mmHg, preferably within the range of 3 to 40 mmHg.

The condensed vapors, obtained at the head of the column in a ratio with the product fed normally ranging from 0.5/1 to 0.95/1, contain isocyanate with a purity of over 99.5% parts by weight.

In an embodiment of the invention, the liquid remaining at the bottom of the column, which contains isocyanate, products containing urethane functions and by-products of the ureic type, is recycled to the first pyrolysis reactor.

This fraction is fed directly to the first pyrolysis reactor, or is first treated with the alcohol corresponding to the R' alkyl group in formula (II) of the urethane to transform the isocyanate functions into urethane functions and is then fed to the above reactor.

This treatment is carried out in a stirred reactor at a temperature within the range of 25° C. to 90° C. for a time ranging from 0.5 to 3 hours, using the alcohol in a weight ratio with the liquid to be treated ranging from 2:1 to 10:1.

The integrated process for the preparation of aromatic isocyanates according to the main object of the present invention, as well as the procedures for effecting the intermediate phases thereof, which also apply to contexts outside that defined herein, and, in turn, also object of the present invention, can be more clearly understood from the following examples which are provided for illustrative purposes and do not limit the scope of the invention.

EXAMPLE 1

Synthesis of Toluenediurethane from the Corresponding Toluenediamine

With reference to FIG. 1, 165 g (1.352 moles) of toluenediamine 80/20 (TDA 80/20, mixture of 2,4- and 2,6- isomers in a proportion of 80/20), 1600 g of dimethylcarbonate (DMC, weight ratio DMC/TDA equal to 9.7) and 8.9 g of zinc acetate dihydrate (0.040 moles, 5.4% by weight with respect to the TDA 80/20, molar ratio catalyst/TDA 80/20 equal to 0.03), are charged into a cylindrical steel autoclave (A) with a useful volume of 3 liters. The autoclave is then pressurized with nitrogen at 2.5 absolute atmospheres, heated so as to maintain an internal temperature of 160° C. for 1.5 hours and stirred at about 300 rpm.

The condenser B is brought to a temperature of 120° C., whereas the condenser C is cooled to a temperature of 5° C.

After 1.5 hours the connection between the autoclave and the condenser B is intercepted, the internal temperature is brought to 175° C. for the following 2 hours (finishing phase).

The maximum pressure registered during the test proved to be equal to 9 absolute atm.

The reaction is left to cool to 120° C. and a quantity of water equal to 1.5 g is added. The mixture is maintained under stirring at 120° C. for about 30 minutes, after which filtration is effected on an F1 sintered steel filter, having an average pore diameter equal to 2 microns (pressure about 5 absolute atm.).

In this way, after evaporation at reduced pressure of the solvent DMC, a raw product is obtained having a weight of 317 g, consisting of 302 g of toluenediurethane 80/20 (mixture in a proportion 80/20 of the respective carbamates of TDA 80/20) and a mixture of by-products having a weight of 15 g.

At the end of the reaction, a quantity of distillate equal to 350 g was collected, of which 86.5 g of methanol, 6 g of methyl acetate and 257.5 g of dimethylcarbonate.

From these results, the following yield, conversion and selectivity values can be calculated:

conversion with respect to the starting TDA 80/20>99% selectivity to toluenediurethane 80/20 equal to 94% yield equal to 94%.

The content of metal zinc residue in the urethane proved to be 15 ppm.

EXAMPLE 2

Comparative

The reaction is carried out under the same operating conditions as example 1, using the same quantity of reagents.

At the end of the reaction, the autoclave is cooled to about 120° C., filtering on a filter thermostat-regulated at the same temperature as the autoclave.

The raw product collected is subsequently distilled at reduced pressure to completely remove the solvent. In this way, a solid residue is obtained of about 270 g. From the HPLC analysis effected, it is possible to calculate the following yield, conversion and selectivity values:

conversion with respect to the starting TDA 80/20≧99% selectivity to toluenediurethane 80/20 equal to 94% yield equal to 94%.

The content of metal zinc residue in the urethane proved to be 1000 ppm.

EXAMPLE 3

Passivation Treatment of the Urethane Catalytic Residues 300 g of toluene dimethylurethane (hereafter TDU) containing 15 ppm of zinc, having a titer of 94% by weight and containing the two 2,4 toluene dimethylurethane and 2,6 toluene dimethylurethane isomers in a weight ratio 80/20, are charged into a cylindrical steel autoclave, having a useful volume of 3 liters.

1650 ml of dimethylcarbonate and 12 mg of $H_3PO_4$ at 85% are also charged into the autoclave and the mixture is maintained under stirring for 2 hours at a temperature of 130° C.

At the end of the treatment, the autoclave is cooled, emptied and the solvent is removed by distillation at reduced pressure.

EXAMPLE 4

Pyrolysis of Urethane in Gas Phase

Figure 2:
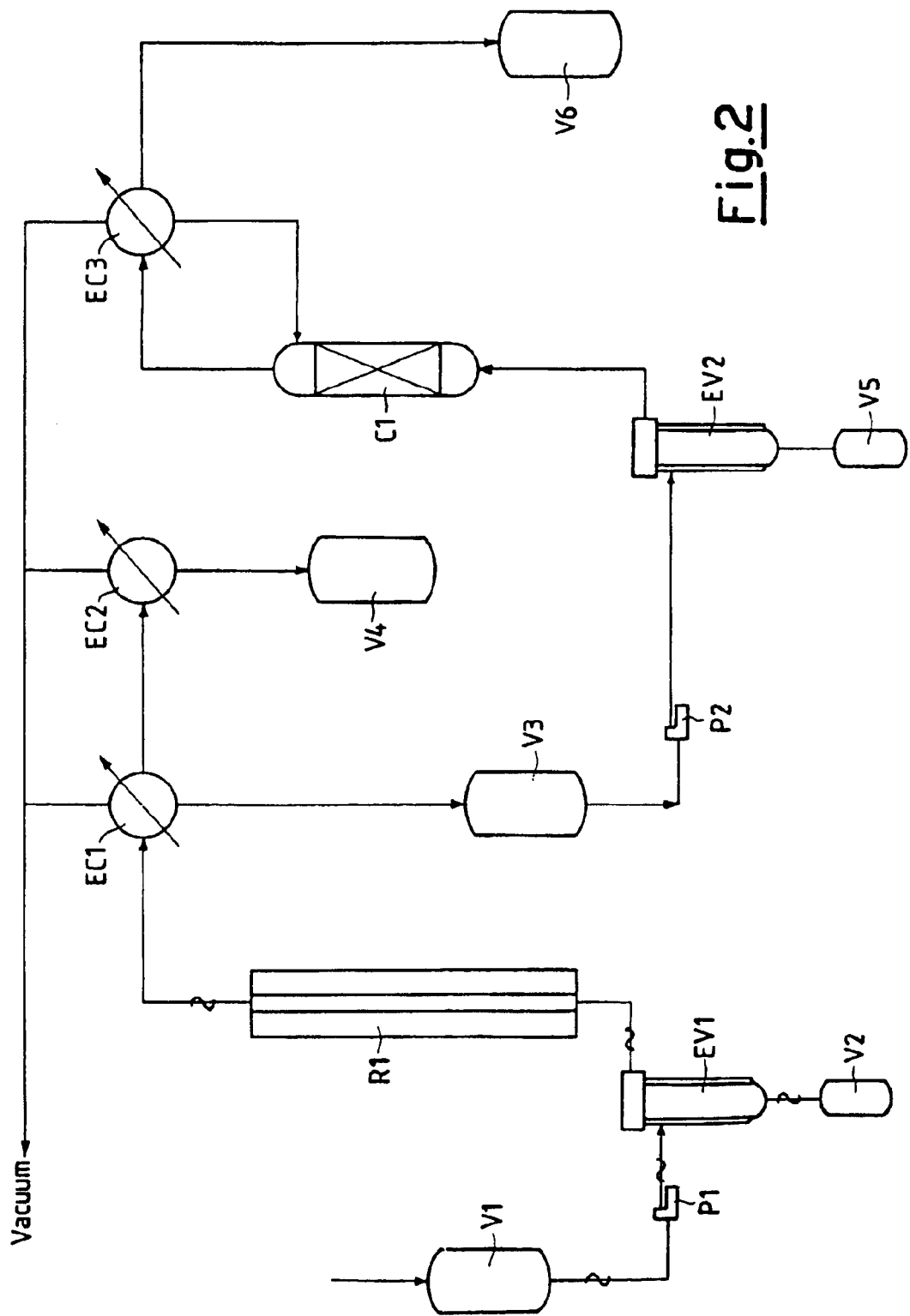
FIG. 2 is a repesentation of apparatus and flow process used for pyrolysis of a urethane in a gas phase.

The pyrolysis step is carried out in the apparatus, illustrated in FIG. 2, consisting of:
1. A melter (V1) of the urethane.
2. A dosage pump of the urethane (P1).
3. A fine film evaporator (EV1) in which the urethane is evaporated, with an exchange surface of 2.2 dm².
4. A tubular cracking reactor (R1) made of Aisi 316L stainless steel having a length of 1000 mm, an internal diameter of 24.8 mm, filled with chips of the same material.
5. A condenser (EC1) for the condensation of the isocyanate.
6. A condenser (EC2) for the condensation of the methanol.

300 g of TDU (titer 94%) treated with $H_3PO_4$ as described in example 3, are charged into and melted in the melter V1, at a temperature of 175° C. and at atmospheric pressure.

The condenser EC1 is cooled with cooling liquid at T=40° C., EC2 is cooled with cooling liquid at T=−20° C., EV1 is heated with diathermic oil at T=306° C. and R1 is heated electrically at a wall temperature of 456° C.

EV1, R1, EC1, EC2, V2, V3, V4 are brought to residual pressure values of 70 mmHg, measured at the outlet of EV1.

Operating under these conditions, molten TDU is fed by means of P1, with a flow-rate of 297 g/hour and 279 g/hour of mixture are evaporated in EV1.

A liquid stream, equal to 18 g/hour, having the following composition, is collected in V2 from the bottom of EV1:
48.5% by weight of TDU
14% by weight of toluene monourethane monoisocyanate (TMI)

37.5% by weight of heavy by-products (allophanates, ureas).

The gas leaving R1 (279 g/hour) is partially condensed in EC1 and the liquid obtained, equal to 206 g/hour, collected in V3, has the following composition:
89.7% by weight of toluene diisocyanate (TDI)
4% by weight of TMI
6.2% by weight of ureas
0.1% by weight of TDU The non-condensed gas in EC1, equal to 73 g/hour, which mainly contains methanol, is condensed in EC2 and collected in V4.

From the above data, a conversion of TDU equal to 96.8%, a selectivity to TDI of 93.5% and a selectivity to TMI of 4.6%, are calculated, for the pyrolysis.

EXAMPLE 5

Recovery of the Isocyanate

In the final step the TDI is recovered from the mixture collected in V3 of example 4, by means of distillation in the apparatus illustrated in FIG. 2, consisting of:
1. A fine film evaporator (EV2), having an exchange surface of 2 dm$^2$, in which the mixture to be rectified is vaporized.
2. A pump (P2) for the feeding of this mixture to EV2.
3. A distillation column (C1), having an internal diameter of 25 mm, a length of 500 mm, filled with Wilson coils.
4. A condenser (EC3) of the isocyanate.

The condenser EC3 is brought to T=20° C., EV2 is heated to T=125° C. and the whole distillation equipment consisting of EV2, C1, EC3, V5, V6, is brought to a residual pressure value of 5 mmHg.

Operating under these conditions, the mixture contained in V3 is fed to EV2 with a flow-rate of 70 g/hour. The vapor leaving C1 (49 g/hour) is completely condensed in EC3 and the liquid obtained, collected in V6, consists of TBI with a purity of over 99.53 by weight.

A liquid stream, equal to 21 g/h, having the following composition, is collected in V5 from the bottom of EV2:
66.8% by weight of TDI
12.2% by weight of TMI
20.7% by weight of ureas
0.3% by weight of TDU.

From the above data, a recovery yield of TDI equal to 77.5% per passage and a mass balance of the isocyanate equal to 100%, are calculated.

EXAMPLE 6

Comparative

With reference to the equipment illustrated in FIG. 2, 300 g of raw TDU (titer 94%), without treatment, containing 15 ppm of zinc, are charged into and melted in the melter V1 at a temperature of 175° C. and at atmospheric pressure.

Operating under the conditions described in example 3, molten TDU is fed by means of P1 at a flow-rate of 307 g/hour.

After twenty minutes of feeding, there begins to be a difference in pressure between the inlet and outlet of the reactor R1, which after thirty minutes becomes such as to no longer allow the test to be continued. This pressure difference is caused by the progressive fouling of the exit line of the gases from the reactor R1, owing to the formation of by-products which are formed with consistence in the presence of zinc.

The presence of traces of zinc in the TDU also creates the formation of considerable quantities of high-boiling by-products during the evaporation phase of the TDU, which cause significant fouling of the film evaporator.

EXAMPLE 7

Figure 3:
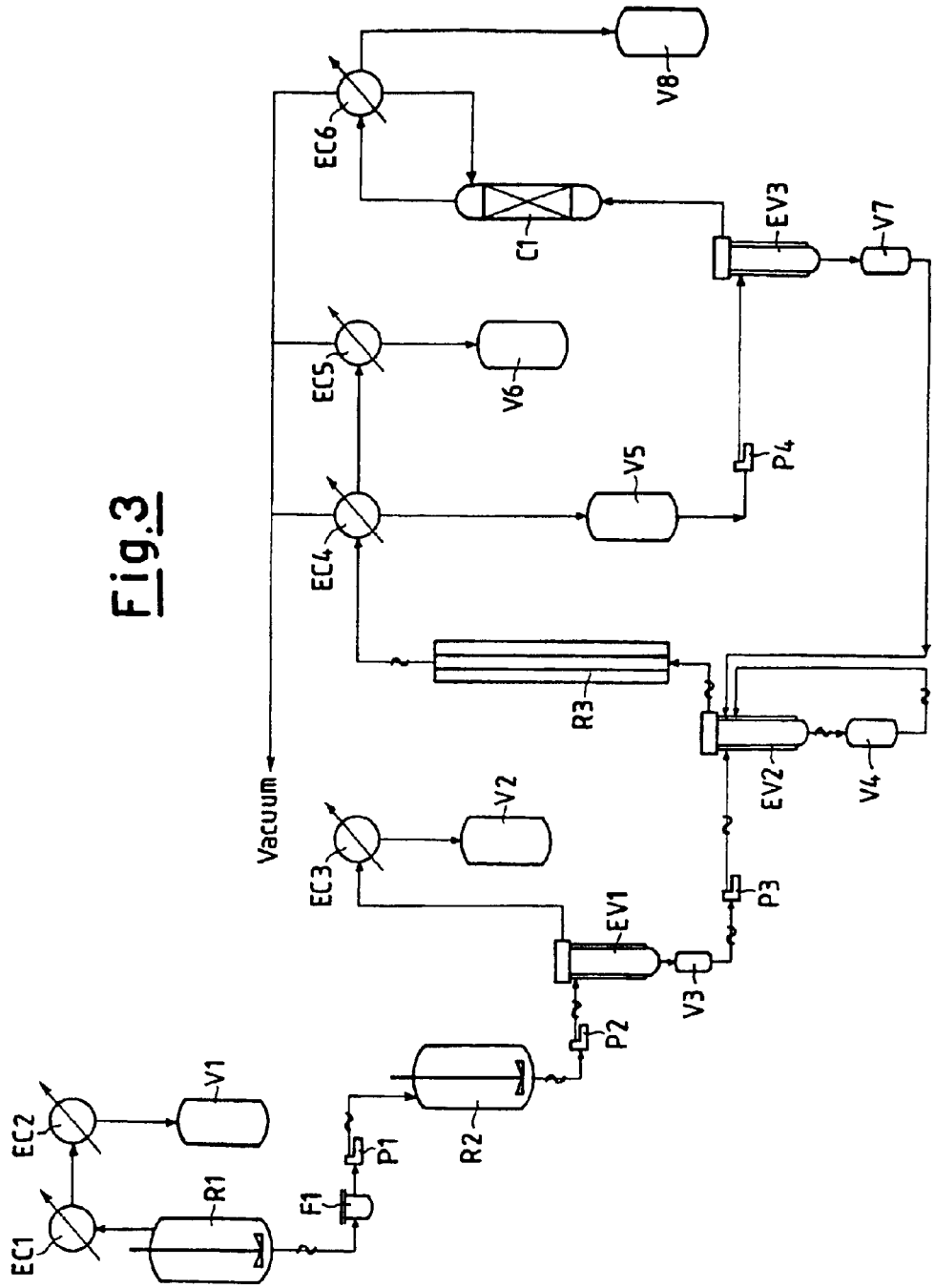
FIG. 3 is a repesentation of equipment and flow process for use in preparing an aromatic isocyanate from the reaction between an aromatic amine and an organic carbonate.

With reference to the equipment illustrated in FIG. 3, 153.4 g (1.257 moles) of toluenediamine 80/20 (TDA 80/20, mixture of 2,4-2,6-isomers in a proportion of 80/20), 1600 g of dimethylcarbonate (DMC, weight ratio DMC/TDA equal to 10.4) and 8.3 g of zinc acetate dihydrate (0.037 moles, 5.4% by weight with respect to the TDA 80/20, molar ratio catalyst/TDA 80/20 equal to 0.03), are charged into the steel reactor R1 having a useful volume of 3 liters. The reactor is then brought to 2.5 absolute atmospheres, heated so as to maintain an internal temperature of 160° C. for 1.5 hours and stirred at about 300 rpm.

The condenser EC1 is brought to a temperature of 120° C., whereas the condenser EC2 is cooled to a temperature of 5° C.

After 1.5 hours the connection between the reactor and condenser EC1 is intercepted, the internal temperature is brought to 175° C. for a further 2 hours (finishing phase).

The maximum pressure registered during the test proved to be equal to 9 absolute atm.

At the end of the reaction, a quantity of distillate equal to 325.5 g was collected, of which 80.5 g of methanol, 5.5 g of methyl acetate and 239.5 g of dimethylcarbonate.

The reaction is left to cool to 120° C. and a quantity of water equal to 1.5 g is added. The mixture is left under stirring at 120° C. for about 30 minutes and is then filtered on a filter F1, made of sintered steel, having an average pore diameter of 2 microns (pressure about 5 absolute atm.).

The reaction mixture thus filtered, consisting of 1360.5 g of DMC, 282 g of toluene dimethylurethane (TDU containing the two isomers 2,4 toluene dimethylurethane and 2,6 toluene dimethylurethane in the weight ratio of 80/20) and 18 g of by-products, is sent by means of P1 to the reactor R2 where 12 mg of $H_3PO_4$ at 85% are added and where the mixture is maintained under stirring for 2 hours at a temperature of 130° C.

At the end of the treatment, the above liquid mixture is fed, by means of P2, with a flow-rate of 350 g/hour to the evaporator EV1 maintained at a temperature of 175° C. and at atmospheric pressure. The dimethylcarbonate is condensed by EC3 and collected in V2, whereas the molten urethane, collected at the bottom of V3, with a titer of 94% by weight and with a zinc content of 15 ppm and a content of dimethylcarbonate of less than 0.5% by weight, is fed by means of P3, with a flow-rate of 297 g/hour, to the evaporator EV2 where 279 g/hour of mixture are vaporized.

The condenser EC4 is cooled with cooling liquid to T=40° C., EC5 is cooled with cooling liquid to T=−20° C., EV2 is heated with diathermic oil to T=306° C. and R3 is electrically heated to a wall temperature of 456° C.

EV2, R3, EC4, EC5, V4, V5, V6 are brought to a residual pressure value of 70 mmHg, measured at the outlet of EV2.

A liquid stream, equal to 18 g/hour, having the following composition, is collected in V4 from the bottom of EV2:
48.5% by weight of TDU
14% by weight of toluene monourethane monoisocyanate (TMI)
37.5% by weight of heavy by-products (allophanates, ureas).

The gas leaving R3 (279 g/hour) is partially condensed in EC4 and the liquid obtained, equal to 206 g/hour, collected in V5, has the following composition:
89.7% by weight of toluene diisocyanate
4% by weight of TMI
6.2% by weight of ureas
0.1% by weight of TDU.

The non-condensed gas in EC4, equal to 73 g/hour, containing methanol, is condensed in EC5 and collected in V6.

In the final step, the TDI is recovered from the mixture collected in V5 by distillation in the apparatus illustrated in FIG. 3 and already described in example 5.

The condenser EC6 is brought to T=20° C., EV3 is heated to T=125° C. and all the distillation equipment consisting of EV3, C1, EC6, V7, V8, is maintained at a residual pressure value of 5 mmHg.

Operating under these conditions, the mixture contained in V5 is fed to EV3, by means of P4, with a flow-rate of 70 g/hour. The vapor leaving C1 (49 g/hour) is completely condensed in EC6 and the liquid obtained, collected in V8, consists of TDI with a purity of over 99.5% by weight.

A liquid stream, equal to 21 g/h, having the following composition, is collected in V7 from the bottom of EV3:
66.8% by weight of TDI
12.2% by weight of TMI
20.7% by weight of ureas
0.3% by weight of TDU.

What is claimed is:

1. An integrated process for the preparation of aromatic isocyanates comprising:
   (a) a reaction between an aromatic amine and an organic carbonate, optionally in the presence of a solvent that is inert with respect to reagents under operating conditions, in the presence of a catalyst selected from organic and inorganic salts of a metal selected from Zn, Sn, Pb, Cu to form an aromatic urethane and an alcohol;
   (b) removal of the catalyst;
   (c) passivation of the residual quantities of metal in the aromatic urethane formed in step (a);
   (d) removal of the solvent and optionally recycling it to step (a) of the reaction;
   (e) evaporation of the aromatic urethane with partial pyrolysis;
   (f) complete pyrolysis of the urethane in gas phase to form an aromatic isocyanate; and
   (g) recovery of the aromatic isocyanate.

2. The integrated process for the preparation of aromatic isocyanates according to claim 1, wherein the aromatic amine fed to the initial reaction with the organic carbonate corresponds to the formula:

R—(NH$_2$)$_n$ wherein n is an integer ranging from 1 to 2, R represents an aryl radical, as such or containing one or more substituents selected from alkyl radicals having up to 4 carbon atoms, or alternatively atoms or radicals inert with respect to the isocyanate function, selected from halogens, alkoxy, nitro, cyano, acyl, acyloxy, isocyanate groups.

3. The integrated process for the preparation of aromatic isocyanates according to claim 1, wherein the aromatic amine contains at least one member selected from a group consisting of 2,4-diaminotoluene, 2,6-diaminotoluene, aniline, toluidine, 3,5-dichloroaniline, 4,4'-methylenedianiline, 2,4'-methylenedianiline, 2,2-methylenedianiline or mixtures of the above isomers.

4. The integrated process for the preparation of aromatic isocyanates according to claim 1, wherein the organic carbonate is selected from alkyl esters of carbonic acid, with the ester group containing an alkyl group having up to 6 carbon atoms.

5. The integrated process for the preparation of aromatic isocyanates according to claim 1, wherein the reaction between the aromatic amine and the organic carbonate is carried out in the presence of a catalyst selected from anhydrous or dihydrate zinc carboxylates, copper base carbonates, zinc base carbonate, mixed zinc and copper carbonates, zinc carbamates.

6. The integrated process for the preparation of aromatic isocyanates according to claim 1, wherein the solvent is selected from alkylated and non-alkylated aromatic hydrocarbons, aromatic hydrocarbons containing functional groups inert to the reagents, alkanes as such or containing functional groups inert to the reagents.

7. The integrated process for the preparation of aromatic isocyanates according to claim 1, wherein the reaction between the aromatic amine and the organic carbonate is carried out in the presence of a quantity of catalyst ranging from 20 to 0.5% in moles per mole of amine.

8. The integrated process for the preparation of aromatic isocyanates according to claim 1, wherein the reaction between the aromatic amine and the organic carbonate is followed by the removal of the mixture consisting of the alcohol by-product and the excess organic carbonate, and by the subsequent separation of this mixture with the organic carbonate recycled to the reaction itself.

9. The integrated process for the preparation of aromatic isocyanates according to claim 1, wherein the removal of the catalyst used in the reaction between the aromatic amine and the organic carbonate is favored by the addition of water.

10. The integrated process for the preparation of aromatic isocyanate according to claim 1, wherein the removal of the catalyst in step (b) is preceded by the addition of water after step (a) to favor the removal of the catalyst before the recovery of the urethane.

11. The process for the synthesis of aromatic urethanes according to claim 10 wherein the water is added in a quantity ranging from 0.5 to 10 moles per mole of catalyst initially charged.

12. The process for the synthesis of aromatic urethanes according to claim 10, wherein the water is added directly to the reaction mixture at temperatures ranging from 100 to 200° C. and at a pressure ranging from 2 to 15 absolute atm.

13. The integrated process for the preparation of aromatic isocyanates according to claim 1, wherein the passivation of the catalytic residues is effected by treatment of the urethane formed with an acid selected from phosphoric and oxalic acid.

14. The integrated process for the preparation of aromatic isocyanates according to claim 13, wherein, when effecting the treatment with phosphoric acid, the urethane containing catalytic residues is dissolved in a low-boiling solvent in a weight ration with respect to the urethane ranging from 1:1 to 10:1.

15. The integrated process for the preparation of aromatic isocyanates according to claim 1, wherein the aromatic urethane obtained down-stream of the passivation of the catalytic residues and removal of the solvent is subjected, in the molten state or in solution, to an evaporation treatment with partial pyrolysis and to subsequent pyrolysis in gas phase.

16. The process according to claim 1, wherein step (f) produces a mixture of vapors that are subsequently subjected to a fractional condensation process as part of step (g); said tractional condensation process comprising at least two steps, the first condensation step being carried out at a temperature of from 20–100° C.

* * * * *